United States Patent
Qiao et al.

(10) Patent No.: US 12,336,736 B2
(45) Date of Patent: Jun. 24, 2025

(54) MINIMALLY INVASIVE FRACTURE REDUCTION AND FIXATION SYSTEM

(71) Applicant: SHAANXI JURENGU MEDICAL EQUIPMENT CO., LTD, Shaanxi (CN)

(72) Inventors: Feng Qiao, Shaanxi (CN); Xiaohang Yang, Shaanxi (CN); Ning Zhang, Shaanxi (CN)

( * ) Notice: Subject to any disclaimer, the term of this patent is extended or adjusted under 35 U.S.C. 154(b) by 0 days.

(21) Appl. No.: 18/841,605

(22) PCT Filed: Apr. 10, 2024

(86) PCT No.: PCT/CN2024/086915
§ 371 (c)(1),
(2) Date: Aug. 26, 2024

(87) PCT Pub. No.: WO2024/170005
PCT Pub. Date: Aug. 22, 2024

(65) Prior Publication Data
US 2025/0120745 A1   Apr. 17, 2025

(30) Foreign Application Priority Data
Oct. 11, 2023   (CN) .......................... 202311313041.1

(51) Int. Cl.
*A61B 17/64* (2006.01)
(52) U.S. Cl.
CPC ................... *A61B 17/645* (2013.01)
(58) Field of Classification Search
CPC .... A61B 17/645; A61B 17/6483; A61B 17/66
See application file for complete search history.

(56) References Cited

U.S. PATENT DOCUMENTS

| | | | | |
|---|---|---|---|---|
| 2005/0043730 A1* | 2/2005 | Janowski | ............. | A61B 17/645 606/56 |
| 2010/0222778 A1* | 9/2010 | Bagnasco | ............. | A61B 17/66 606/58 |
| 2011/0172664 A1* | 7/2011 | Bagnasco | ............. | A61B 17/66 606/59 |

FOREIGN PATENT DOCUMENTS

| CN | 11300901 A | | 7/2021 |
|---|---|---|---|
| CN | 214180559 U | * | 9/2021 |

OTHER PUBLICATIONS

Translation of CN-214180559-U (Year: 2021).*

(Continued)

*Primary Examiner* — Julianna N Harvey
(74) *Attorney, Agent, or Firm* — Addison D. Ault; IPGentleman Intellectual Property Services, LLC (57) ABSTRACT

The present disclosure discloses a minimally invasive fracture reduction and fixation system, including a retractable fixing bracket, a reduction device and a fixing device, wherein the retractable fixing bracket includes a connecting member, and a first fixing member and a second fixing member, the reduction device includes at least two reduction regulators, internal fixing needles and limit sleeves, each reduction regulator includes an outer sleeve and an inner sleeve, the inner sleeve has a center hole matching the internal fixing needle at its center, and the fixing device includes at least two external fixing needles. The present disclosure can realize longitudinal displacement and transverse displacement of the first bone segment and the second bone segment of the fracture with reference to the anteroposterior direction, and can realize minimally invasive reduction of the first bone segment and the second bone segment of the fracture.

4 Claims, 8 Drawing Sheets

(56) References Cited

OTHER PUBLICATIONS

CNIPA CN202311313041.1 First Office Action, Feb. 8, 2024, Original chinese, pp. 1-6.
CNIPA CN202311313041.1 First Office Action, Feb. 8, 2024, English machine translation, generated Aug. 25, 2024, pp. 1-5.

* cited by examiner

MINIMALLY INVASIVE FRACTURE REDUCTION AND FIXATION SYSTEM

CROSS-REFERENCE TO RELATED APPLICATION

This application is a Section 371 National Stage Application of International Application No. PCT/CN2024/086915, filed on Apr. 10, 2024, entitled "Minimally invasive fracture reduction and fixation system", which claims priority to Chinese Application No. 202311313041.1, filed on Oct. 11, 2023, incorporated herein by reference in their entirety.

TECHNICAL FIELD

The present disclosure relates to the field of medical device, and in particular to a minimally invasive fracture reduction and fixation system.

BACKGROUND

Limb fracture is a common clinical disease. Good reduction and proper fixation are important guarantees for obtaining good limb function. Fracture reduction has always been a difficult problem that plagues clinical practice. Although open reduction is relatively easy, it is traumatic, destroys soft tissues such as periosteum, affects fracture healing, and is prone to infection and secondary fracture. Therefore, when treating fractures clinically, closed minimally invasive fracture reduction is used as much as possible. However, closed reduction requires repeated fluoroscopy, which increases the radiation damage of X-rays. In addition, the fixation method of the fracture determines the healing effect of the fracture. If the fixation is not firm, it will affect the fracture healing. If the fixation is too strong, it will also affect the fracture healing. Therefore, different fixation methods should be used at different stages of fracture healing. In the early stage, strong fixation is suitable, in the middle stage, pressure fixation is suitable, and in the late stage, elastic fixation is suitable. However, it is difficult to achieve the conversion of several fixation methods with the currently commonly used orthopedic external fixators, which may cause fracture displacement. At present, the internationally recognized orthopedic external fixators or orthopedic external fixation frames are not only cumbersome to operate, unreliable in fixation, large in size, and inconvenient for postoperative care, but also inconvenient for postoperative pressurization and adjustment, and may even cause fracture displacement, etc., affecting fracture healing. Furthermore, there are clear clinical healing standards for fractures in the world, but in clinical practice, it is impossible to implement it. The facts of whether the fracture is healed and whether the healing is firm depend entirely on the doctor's experience. There is no standard for when to remove the external fixator. In order to avoid serious complications of re-fracture, the time of wearing the fixator can only be extended. Therefore, a minimally invasive reduction and fixation system for fractures should be provided.

SUMMARY

The technical problem to be solved by the present disclosure is to provide a minimally invasive reduction and fixation system for fractures in view of the deficiencies in the above-mentioned prior art. The system has a simple structure and a reasonable design. The connection between the first bone segment and the second bone segment of the fracture can be achieved by using a retractable fixing bracket. By adjusting the length of the retractable fixing bracket, the first bone segment and the second bone segment of the fracture can be longitudinally displaced in the anteroposterior direction. The reduction device can be used to laterally displace the first bone segment and the second bone segment of the fracture relative to the anteroposterior direction. Thereby, minimally invasive reduction of the first bone segment and the second bone segment of the fracture is achieved.

In order to solve the above technical problem, the technical solution adopted by the present disclosure is: A minimally invasive fracture reduction and fixation system, comprising a retractable fixing bracket, and a reduction device and a fixing device mounted on the retractable fixing bracket, wherein the retractable fixing bracket comprises a connecting member, and a first fixing member and a second fixing member respectively mounted on both ends of the connecting member, the reduction device comprises at least two reduction regulators respectively mounted on the first fixing member and the second fixing member, internal fixing needles inserted into the reduction regulators and limit sleeves fixedly sleeved on the internal fixing needles, each reduction regulator comprises an outer sleeve and an inner sleeve threadedly connected to the outer sleeve, the inner sleeve has a center hole matching the internal fixing needle at its center, and the fixing device comprises at least two external fixing needles respectively mounted on the first fixing member and the second fixing member.

According to some embodiments of the present disclosure, the outer sleeve comprises a large-diameter cylindrical sleeve section, a threaded sleeve section and a small-diameter cylindrical sleeve section coaxially arranged in sequence, and the threaded sleeve section is threadedly connected to the first fixing member or the second fixing member.

According to some embodiments of the present disclosure, the inner sleeve comprises a guide pipe section, a connecting pipe section and a nut coaxially arranged in sequence, and the connecting pipe section is threadedly connected to the large-diameter cylindrical sleeve section.

According to some embodiments of the present disclosure, both the first fixing member and the second fixing member are lockable on the connecting member by respective fastening bolts, the connecting member is provided with waist-shaped holes for the fastening bolts to pass through, and the first fixing member and the second fixing member are each provided with a fastening bolt mounting hole.

According to some embodiments of the present disclosure, the first fixing member and the second fixing member are each provided with a threaded sleeve section mounting hole.

According to some embodiments of the present disclosure, the limit sleeve is fixedly sleeved on the internal fixing needle by a fastening screw.

According to some embodiments of the present disclosure, a guide slide slot is provided in the connecting member, and the first fixing member and the second fixing member are each provided with a guide protrusion matching the guide slide slot.

Compared with the prior art, the present disclosure has the following advantages:

I. The present disclosure provides a reduction device on the retractable fixing bracket, and the reduction device includes at least two reduction regulators, internal fixing needles and limit sleeves. The reduction regulator includes an outer sleeve and an inner sleeve, and the center of the inner sleeve has a center hole. In actual use, the retractable fixing bracket can be used to achieve the connection between the first bone segment and the second bone segment of the fracture. By adjusting the length of the retractable fixing bracket, the first bone segment and the second bone segment of the fracture can be longitudinally displaced in the anteroposterior direction. The reduction device can be used to laterally displace the first bone segment and the second bone segment of the fracture relative to the anteroposterior direction. Thereby, it achieves minimally invasive reduction of the first bone segment and the second bone segment of the fracture.

II. The present disclosure provides a fixing device on the retractable fixing bracket, and the fixing device includes at least two external fixing needles, and the at least two external fixing needles are respectively installed on the first fixing member and the second fixing member. In actual use, after completing the reduction of the first bone segment and the second bone segment of the fracture, external fixing needles for positioning are respectively installed on the first fixing member and the second fixing member in turn, and the connections between the retractable fixing bracket and the first bone segment and the second bone segment of the fracture are realized by using the two external fixing needles. After that, by adjusting the length of the retractable fixing bracket again, the two external fixing needles are used to perform the final reduction between the first bone segment and the second bone segment of the fracture. When the final reduction meets the requirements, all the internal fixing needles can be pulled out, all the reduction regulators can be removed, and one or two external fixing needles can be respectively installed on the first fixing member and the second fixing member again to realize the final fixation between the retractable fixing bracket and the first bone segment and the second bone segment of the fracture.

III. The reduction regulator of the present disclosure has a clever structure, is easy to operate, and has high adjustment accuracy.

In summary, the present disclosure has a simple structure and a reasonable design, and it can realize longitudinal displacement and transverse displacement of the first and second bone segments of the fracture with reference to the anteroposterior direction, and can realize minimally invasive reduction of the first and second bone segments of the fracture.

The present disclosure will be further described in detail below through the accompanying drawings and embodiments.

DESCRIPTION OF THE REFERENCE NUMERALS

| 1 - connecting member; | 1-1 - waist-shaped hole; | 1-2 - guide slide slot; |
|---|---|---|
| 2 - first fixing member; | 3 - second fixing member; | 4 - fastening bolt; |
| 5 - fastening bolt mounting hole; | 6 - threaded sleeve section mounting hole; | 7-1 - large-diameter cylindrical sleeve section; |
| 7-2 - threaded sleeve section; | 7-3 - small-diameter cylindrical sleeve section; | 8-1 - guide pipe section; |
| 8-2 - connecting pipe section; | 8-3 - nut; | 8-4 - center hole; |
| 9 - internal fixing needle; | 10 - limit sleeve; | 11 - fastening screw; |
| 12 - external fixing needle; | 13-1 - first bone segment; | 13-2 - second bone segment. |

DETAILED DESCRIPTION OF EMBODIMENTS

Figure 1:
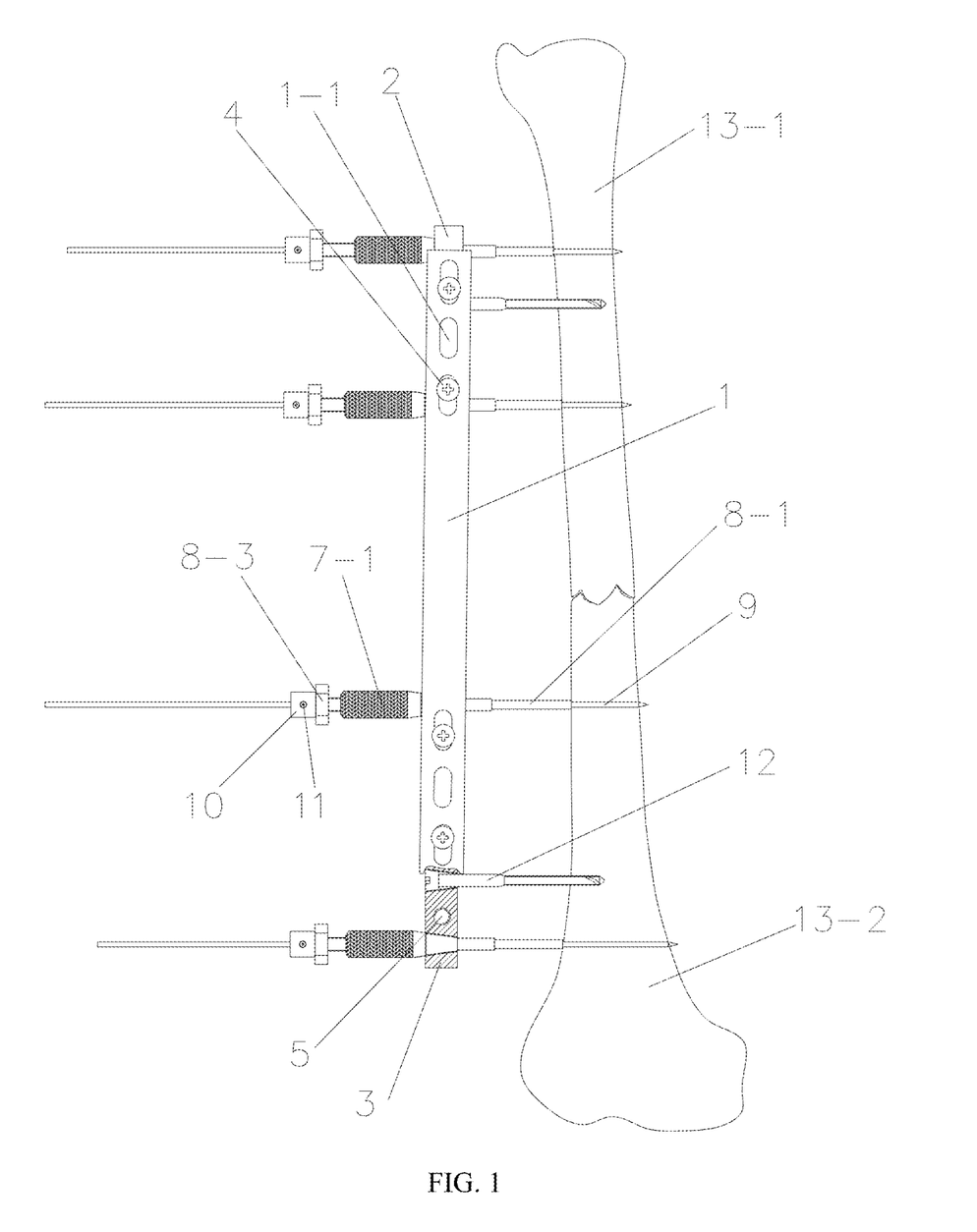
FIG. 1 is a schematic view of the use state of the present disclosure in a front view.
Figure 2:
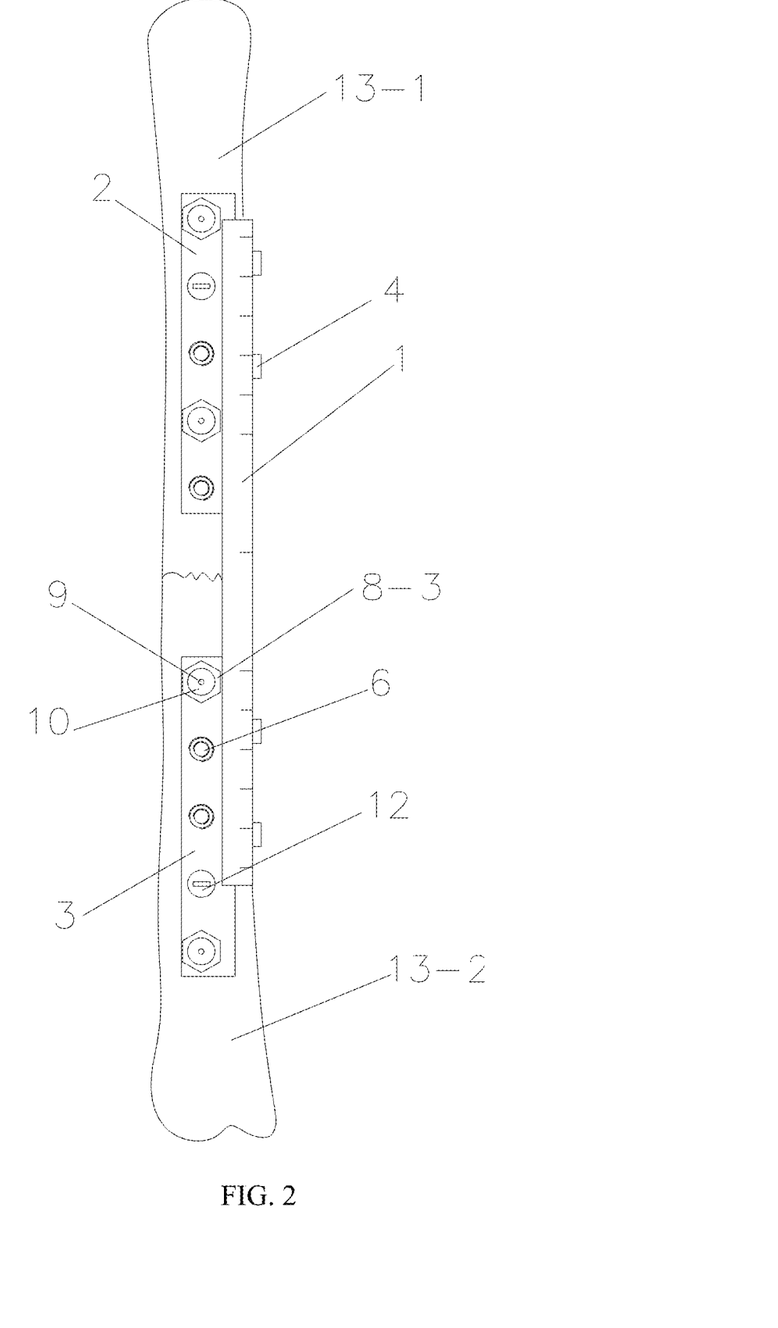
FIG. 2 is a schematic view of the use state of the present disclosure in a side view.

As shown in FIGS. 1 and 2, a minimally invasive fracture reduction and fixation system comprises a retractable fixing bracket, and a reduction device and a fixing device installed on the retractable fixing bracket, wherein the retractable fixing bracket comprises a connecting member 1, and a first fixing member 2 and a second fixing member 3 respectively installed at both ends of the connecting member 1, the reduction device comprises at least two reduction regulators respectively installed on the first fixing member 2 and the second fixing member 3, internal fixing needles 9 inserted in the reduction regulators and limit sleeves 10 fixedly sleeved on the internal fixing needles 9, each reduction regulator comprises an outer sleeve and an inner sleeve threadedly connected to the outer sleeve, the center of the inner sleeve has a center hole 8-4 matching the internal fixing needle 9, and the fixing device comprises at least two external fixing needles 12 respectively installed on the first fixing member 2 and the second fixing member 3.

In this embodiment, a reduction device is provided on the retractable fixing bracket, and the reduction device includes at least two reduction regulators, internal fixing needles 9 and limit sleeves 10. The reduction regulator includes an outer sleeve and an inner sleeve, and the center of the inner sleeve has a center hole 8-4. In actual use, the retractable fixing bracket can be used to achieve the connection between the fractured first bone segment 13-1 and second bone segment 13-2. By adjusting the length of the retractable fixing bracket, the fractured first bone segment 13-1 and second bone segment 13-2 are longitudinally displaced in the anteroposterior direction/in the front view. The reduction device can be used to laterally/horizontally displace the fractured first bone segment 13-1 and second bone segment 13-2 relative to the anteroposterior direction (in the front view), thereby achieving minimally invasive reduction of the fractured first bone segment 13-1 and second bone segment 13-2.

As shown in FIG. 1, in this embodiment, the specific operation process of the reduction regulator is as follows: when it is necessary to push the first bone segment 13-1 or the second bone segment 13-2 toward the side away from the connecting member 1, the inner sleeve is screwed counter-clockwise so that one end of the inner sleeve pushes the side of the first bone segment 13-1 or the second bone segment 13-2, thereby pushing the first bone segment 13-1 or the second bone segment 13-2 toward the side away from the connecting member 1; after that, the position of the limit sleeve 10 is adjusted, so that the end surface of the limit sleeve 10 is always in close contact with the other end of the inner sleeve, in this way, the limit sleeve 10 can always limit the position of the inner sleeve; when it is necessary to pull the first bone segment 13-1 or the second bone segment 13-2 toward the side close to the connecting member 1, the inner sleeve is screwed clockwise to make the inner sleeve push the limit sleeve 10 to move away from the first bone segment 13-1 or the second bone segment 13-2; at this time, under the driving action of the limit sleeve 10, the limit sleeve 10 will simultaneously drive the internal fixing needle 9 to move away from the bone.

In this embodiment, a fixing device is provided on the retractable fixing bracket, and the fixing device includes at least two external fixing needles 12, and the at least two external fixing needles 12 are respectively installed on the first fixing member 2 and the second fixing member 3. In actual use, since the internal fixing needle 9 is a Kirschner wire or a titanium needle/pin, after the first bone segment 13-1 and the second bone segment 13-2 of the fracture are reduction, the internal fixing needle 9 needs to be removed, and the external fixing needle 12 needs to be used to fix the reduced first bone segment 13-1 and second bone segment 13-2, so as to facilitate the healing of the first bone segment 13-1 and the second bone segment 13-2 of the fracture. However, it should be noted that after the first bone segment 13-1 and the second bone segment 13-2 of the fracture are reduced, external fixing needles 12 for positioning are respectively installed on the first fixing member 2 and the second fixing member 3 in sequence, and the two external fixing needles 12 are used to realize the connection between the retractable fixing bracket and the first bone segment 13-1 and the second bone segment 13-2 of the fracture. After that, by adjusting the length of the retractable fixing bracket again, the two external fixing needles 12 are used to perform the final reduction between the first bone segment 13-1 and the second bone segment 13-2 of the fracture. When the final reduction meets the requirements, all the internal fixing needles 9 can be pulled out, all the reduction regulators can be removed, and one or two external fixing needles 12 are respectively installed on the first fixing member 2 and the second fixing member 3 again to realize the final fixation between the retractable fixing bracket and the first bone segment 13-1 and the second bone segment 13-2 of the fracture.

Figure 5:
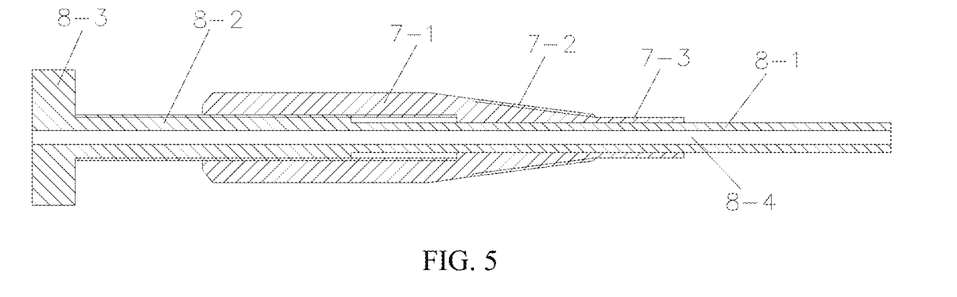
FIG. 5 is a schematic view of the structure of the reduction regulator of the present disclosure.

As shown in FIGS. 1 and 5, in this embodiment, the outer sleeve includes a large-diameter cylindrical sleeve section 7-1, a threaded sleeve section 7-2 and a small-diameter cylindrical sleeve section 7-3 coaxially arranged in sequence, and the threaded sleeve section 7-2 is threadedly connected to the first fixing member 2 or the second fixing member 3.

In this embodiment, the inner sleeve includes a guide pipe section 8-1, a connecting pipe section 8-2 and a nut 8-3 which are coaxially arranged in sequence, and the connecting pipe section 8-2 is threadedly connected to the large-diameter cylindrical sleeve section 7-1.

In this embodiment, through the threaded connection between the connecting pipe section 8-2 and the large-diameter cylindrical sleeve section 7-1, the inner sleeve can be linearly moved in the outer sleeve when the inner sleeve is screwed.

In this embodiment, through the cooperation between the guide pipe section 8-1 and the small-diameter cylindrical sleeve section 7-3, the guide pipe section 8-1 can play a guiding role for the small-diameter cylindrical sleeve section 7-3, and can improve the accuracy of the linear movement of the inner sleeve.

Figure 3:
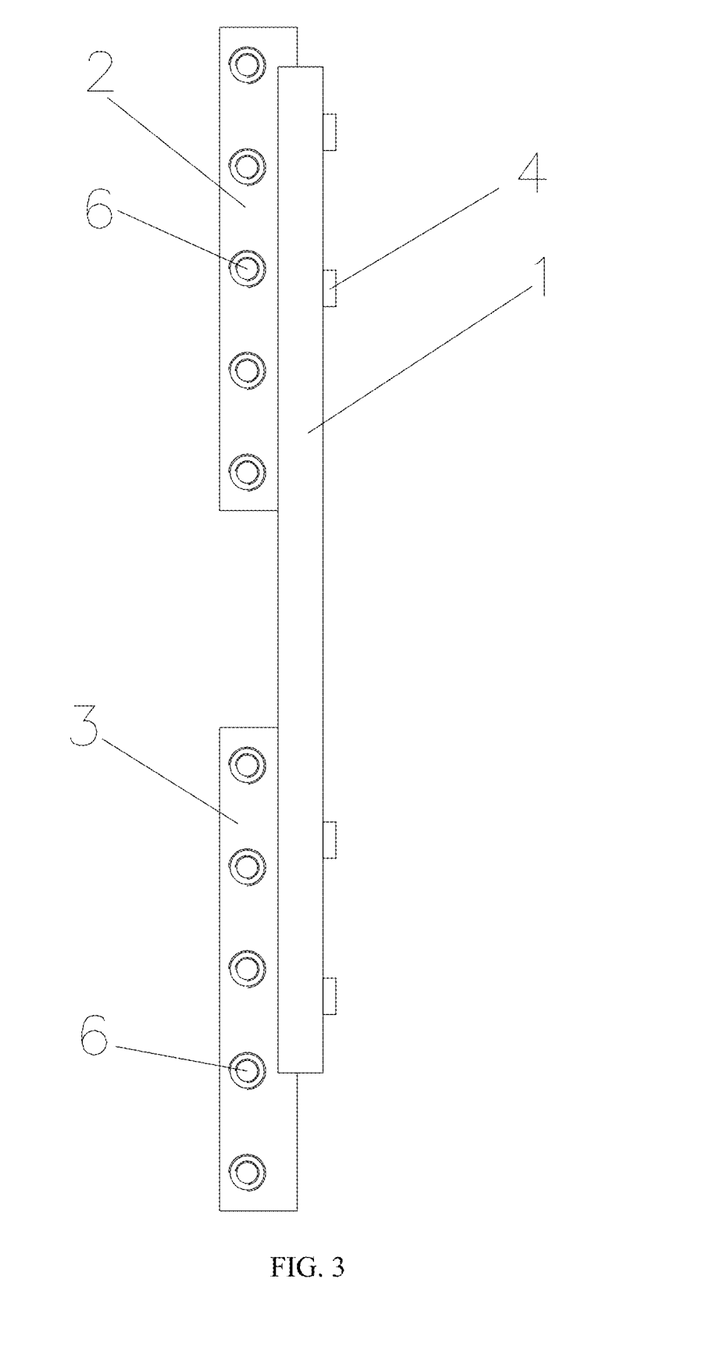
FIG. 3 is a schematic view of the structure of the retractable fixing bracket of the present disclosure.

As shown in FIGS. 1 and 3, both the first fixing member 2 and the second fixing member 3 can be locked on the connecting member 1 by respective fastening bolts 4, and the connecting member 1 is provided with waist-shaped holes 1-1 for the fastening bolts 4 to pass through, and the first fixing member 2 and the second fixing member 3 are each provided with a fastening bolt mounting hole 5.

During actual installation, the length of the retractable fixing bracket can be fine-tuned by adjusting the locking position of the fastening bolt 4 in the waist-shaped hole 1-1.

As shown in FIGS. 1, 3 and 5, in this embodiment, the first fixing member 2 and the second fixing member 3 are each provided with a threaded sleeve section mounting hole 6.

During actual installation, the connection between the outer sleeve and the first fixing member 2 or between the outer sleeve and the second fixing member 3 is achieved by threading the threaded sleeve section 7-2 in the threaded sleeve section mounting hole 6.

As shown in FIG. 1, in this embodiment, the limit sleeve 10 is fixedly sleeved on the internal fixing needle 9 by a fastening screw 11.

Figure 4:
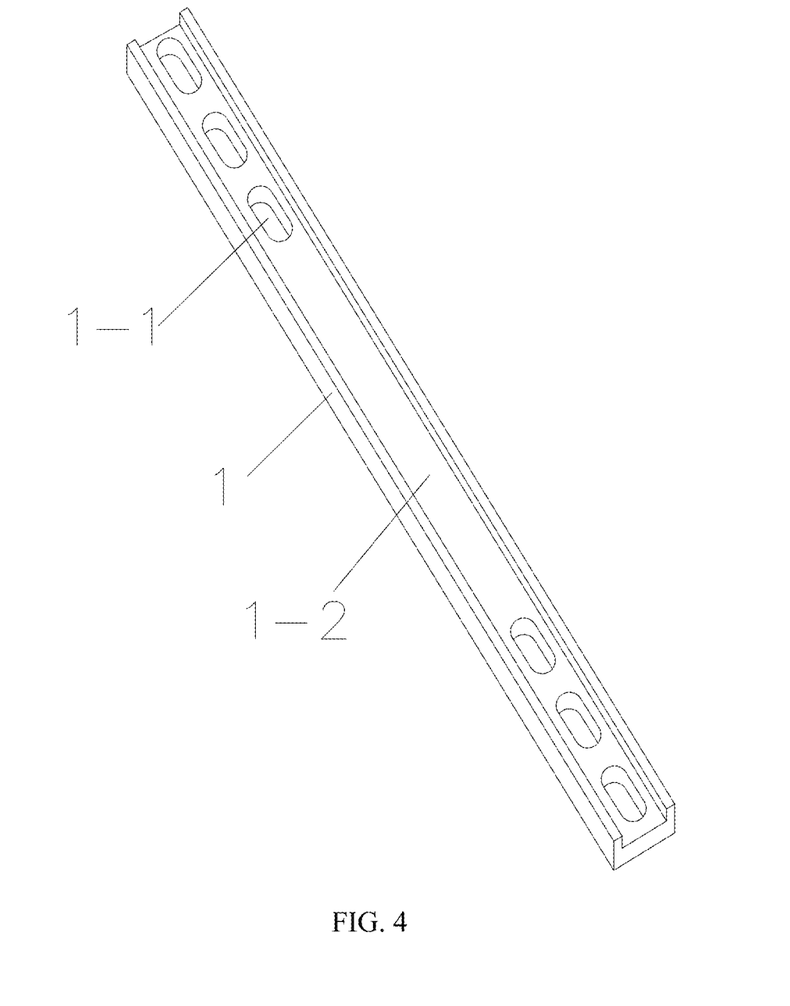
FIG. 4 is a schematic view of the structure of the connecting member of the present disclosure.

As shown in FIGS. 3 and 4, in this embodiment, the connecting member 1 is provided with a guide slide slot 1-2, and the first fixing member 2 and the second fixing member 3 are each provided with a guide protrusion matching the guide slide slot 1-2.

In this embodiment, the guide slide slot 1-2 is a rectangular slide slot, and the first fixing member 2 and the second fixing member 3 are both cuboid fixing members matching the rectangular slide slot.

In actual use, when the fractured first bone segment 13-1 and second bone segment 13-2 need to be reduced, firstly, one or two reduction regulators are installed on the first fixing member 2 and the second fixing member 3, in such a way that one end of the inner sleeve of the reduction regulator installed on the first fixing member 2 is tightly close to the side of the first bone segment 13-1, and one end of the inner sleeve of the reduction regulator installed on the second fixing member 3 is tightly close to the side of the second bone segment 13-2; secondly, an internal fixing needle 9 is drilled into each inner sleeve; then, a limit sleeve 10 is fixedly mounted on each of the internal fixing needles 9, so that the end surface of the limit sleeve 10 is tightly close to the other end of the inner sleeve; at this time, the retractable fixing bracket and the fractured first bone segment 13-1 and second bone segment 13-2 are connected integrally.

If the first bone segment 13-1 and the second bone segment 13-2 form an angle in the side view, it is necessary to first press the fractured first bone segment 13-1 and second bone segment 13-2 externally or lift or press the fractured first bone segment 13-1 and second bone segment 13-2 with a pry bar to eliminate the angle between the fractured first bone segment 13-1 and second bone segment 13-2 in the side view, so that the fractured first bone segment 13-1 and second bone segment 13-2 are both in the same horizontal plane. After that, the displacement in the anteroposterior direction (front view) is adjusted by using the reduction device. By screwing the inner sleeve, the inner sleeve drives the fractured first bone segment 13-1 and second bone segment 13-2 to perform a transverse horizontal displacement in the front view; by adjusting the length of the retractable fixing bracket, the fractured first bone segment 13-1 and second bone segment 13-2 are displaced longitudinally in the anteroposterior direction, so that the gap between the fractured first bone segment 13-1 and second bone segment 13-2 can be eliminated.

Figure 6:
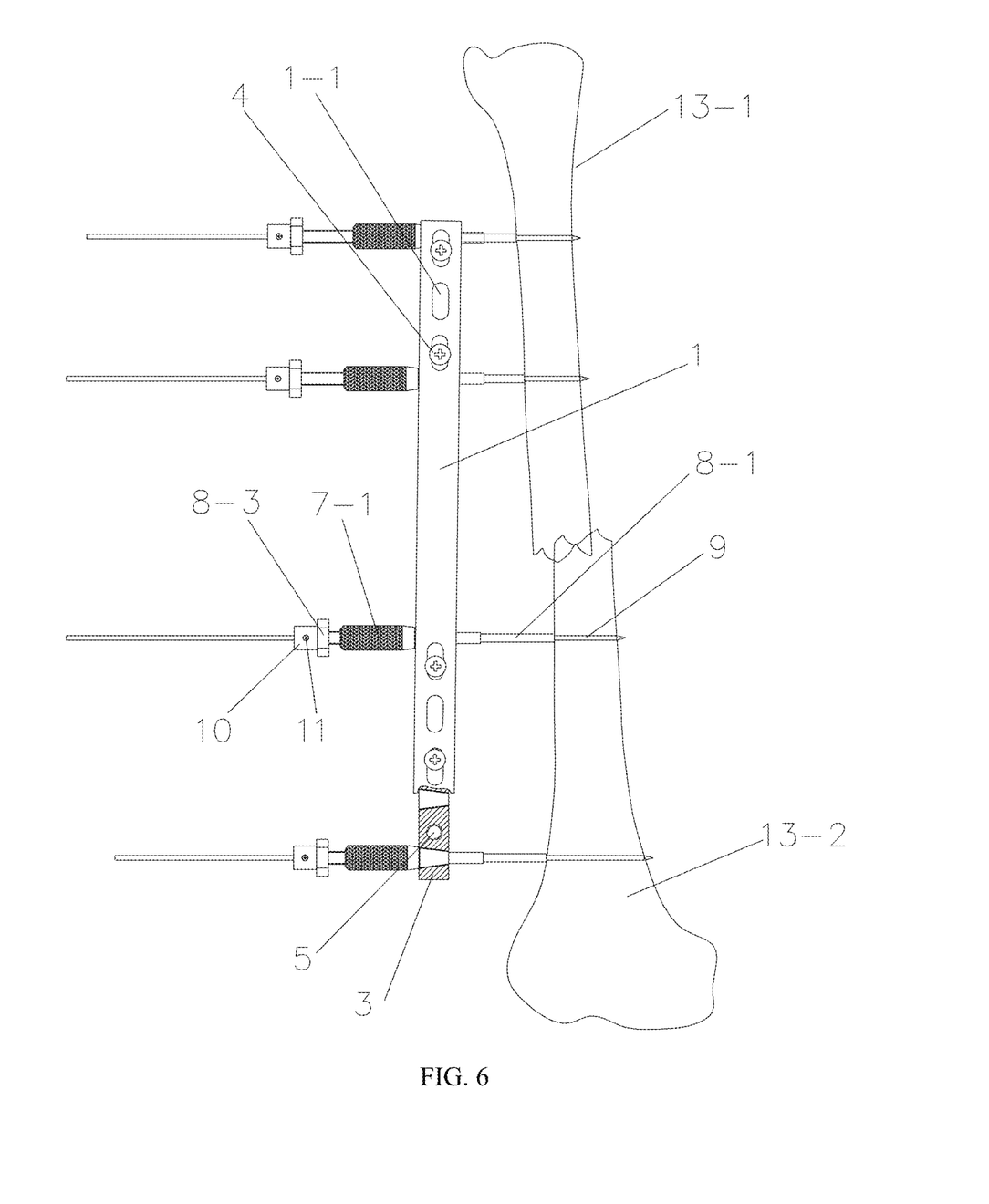
FIG. 6 is a schematic view showing the adjustment of the minimally invasive fracture reduction and fixation system of the present disclosure.

As shown in FIG. 6, when the first bone segment 13-1 and the second bone segment 13-2 are overlapped in the anteroposterior direction, it is necessary to adjust the length of the retractable fixing bracket to eliminate the overlap and displacement between the first bone segment 13-1 and the second bone segment 13-2. The specific operation process is as follows: firstly, loosen the fastening bolt 4 used to connect the first fixing member 2 and the connecting member 1, slide the first fixing member 2 along the guide slide slot 1-2, and eliminate the overlap and displacement between the first bone segment 13-1 and the second bone segment 13-2 by traction or tool pulling, and then, tighten the fastening bolt 4 used to connect the first fixing member 2 and the connecting member 1; if there are still overlap and displacement, loosen the fastening bolt 4 used to connect the second fixing member 3 and the connecting member 1, slide the second fixing member 3 along the guide slide slot 1-2, and eliminate the remaining overlap and displacement between the first bone segment 13-1 and the second bone segment 13-2 by traction or tool pulling, then tighten the fastening bolt 4 used to connect the second fixing member 3 and the connecting member 1. If the overlap and displacement are still not eliminated, the fastening bolt 4 can be removed, and another waist-shaped hole 1-1 at a suitable position on the connecting member 1 can be re-selected to install the fastening bolt 4, so as to achieve a larger extension of the retractable fixing bracket.

Figure 7:
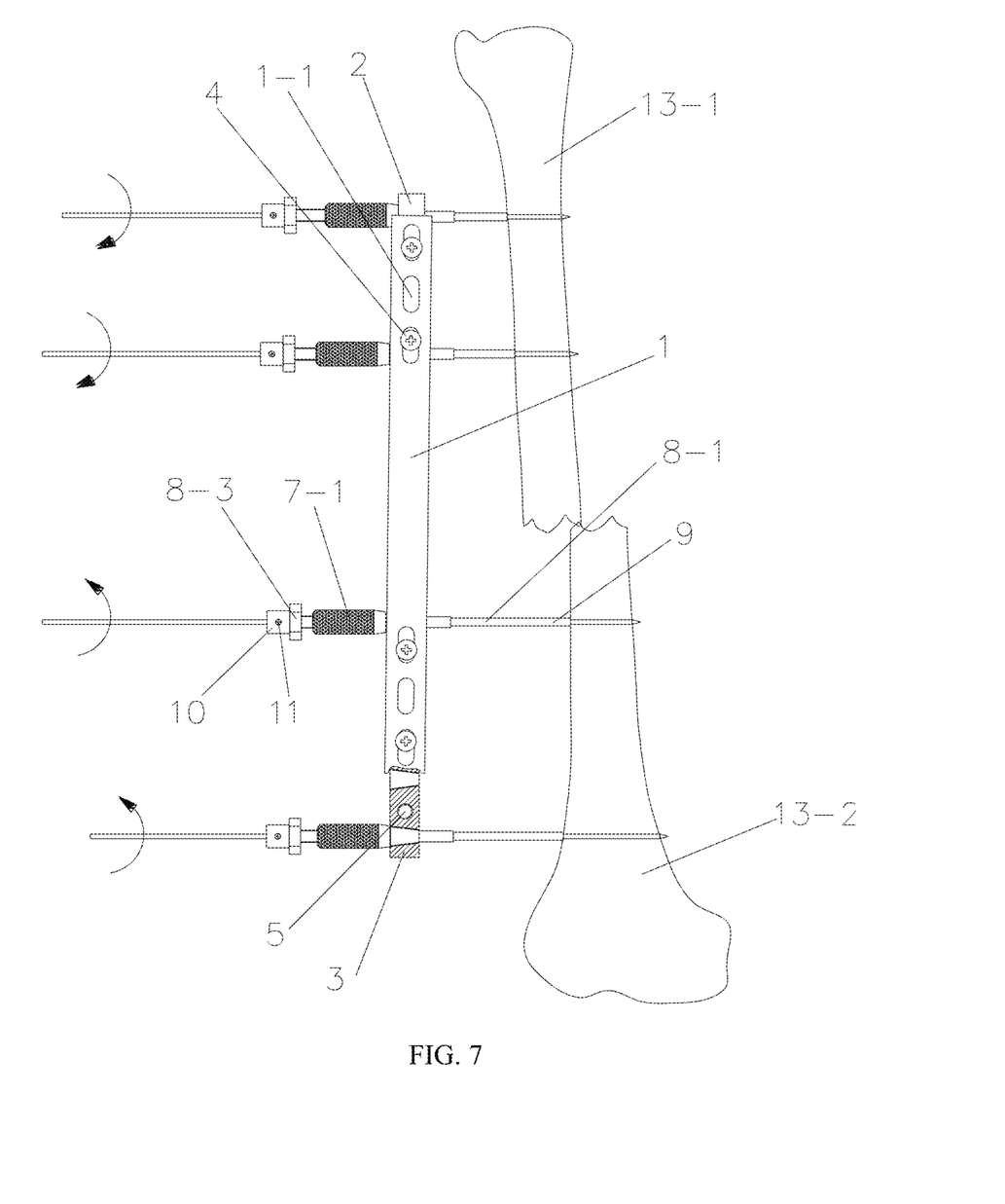
FIG. 7 is a schematic view showing the adjustment of the minimally invasive fracture reduction and fixation system of the present disclosure.

As shown in FIG. 7, if the first bone segment 13-1 and the second bone segment 13-2 are non-angularly displaced/staggered in the anteroposterior direction, the inner sleeves of the two reduction regulators connected to the first fixing member 2 are simultaneously screwed clockwise, so that the inner sleeves of the two reduction regulators simultaneously push the first bone segment 13-1 to translate toward the side away from the connecting member 1 (connecting rod), and the inner sleeves of the two reduction regulators connected to the second fixing member 3 are simultaneously screwed counterclockwise, so that the inner sleeves of the two reduction regulators simultaneously pull the second bone segment 13-2 to translate toward the side close to the connecting member 1, thereby realizing the alignment and reduction of the first bone segment 13-1 and the second bone segment 13-2.

Figure 8:
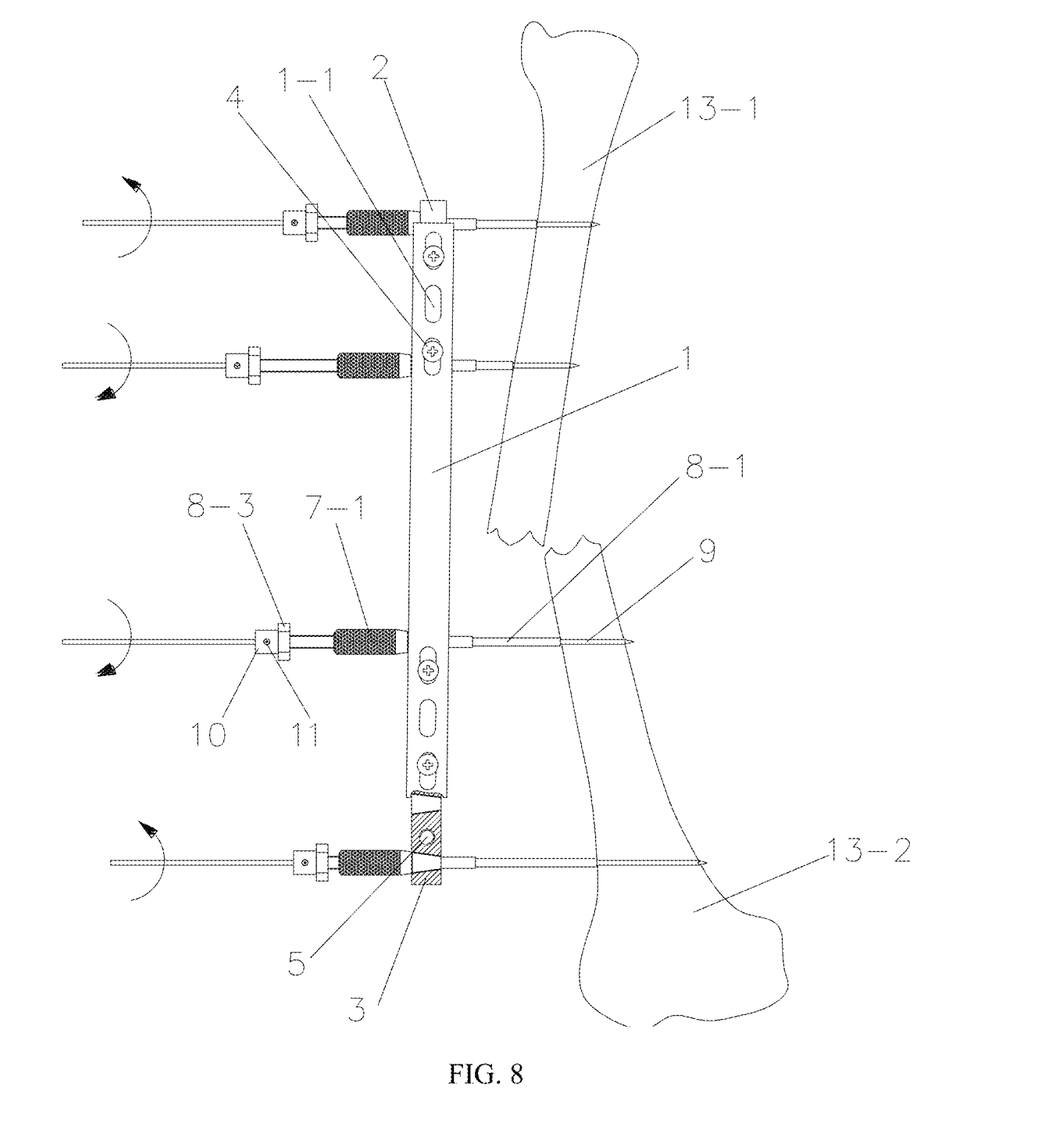
FIG. 8 is a schematic view showing the adjustment of the minimally invasive fracture reduction and fixation system of the present disclosure.

As shown in FIG. 8, in the case where the first bone segment 13-1 and the second bone segment 13-2 are angularly displaced in the anteroposterior direction, since both the first bone segment 13-1 and the second bone segment 13-2 need to be rotated to adjust the angle, the inner sleeves of the two reduction regulators connected to the first fixing member 2 are screwed in opposite directions, that is, the inner sleeve of one reduction regulator needs to be screwed clockwise to push the end of the first bone segment 13-1 close to the connecting member 1 toward the side away from the connecting member 1, and the inner sleeve of the other reduction regulator needs to be screwed counterclockwise to pull the end of the first bone segment 13-1 away from the connecting member 1 toward the side close to the connecting member 1. Similarly, the inner sleeves of the two reduction regulators connected to the second fixing member 3 are screwed in opposite directions, that is, the inner sleeve of one reduction regulator needs to be screwed clockwise to push the end of the second bone segment 13-2 close to the connecting member 1 toward the side away from the connecting member 1, and the inner sleeve of the other reduction regulator needs to be screwed counterclockwise to pull the end of the second bone segment 13-2 away from the connecting member 1 toward the side close to the connecting member 1. Through repeated adjustments, the first bone segment 13-1 and the second bone segment 13-2 are aligned and reduction.

As shown in FIGS. 1 and 2, after the fractured first bone segment 13-1 and second bone segment 13-2 are satisfactorily repositioned/reduced, external fixing needles 12 for positioning are respectively installed between the first fixing member 2 and the first bone segment 13-1, and between the second fixing member 3 and the second bone segment 13-2. After that, all the internal fixing needles 9 are removed. At this time, the first fixing member 2 and the first bone segment 13-1, and the second fixing member 3 and the second bone segment 13-2 are each fixedly connected only by one external fixing needle 12. Due to the large diameter of the external fixing needles 12, the stable fixation between the first fixing member 2 and the first bone segment 13-1, and between the second fixing member 3 and the second bone segment 13-2 can be ensured. Even after all the internal fixing needles 9 are removed, the first bone segment 13-1 and the second bone segment 13-2 may still be in a stable state in the anteroposterior direction. Then, the positions of the first bone segment 13-1 and the second bone segment 13-2 in the lateral direction may be checked again by fluoroscopy and other methods. When there is still displacement/non-alignment in the lateral direction, it is only necessary to complete the reduction and correction of the first bone segment 13-1 and the second bone segment 13-2 in the lateral direction by external pressing or other methods according to the displacement directions of the first bone segment 13-1 and the second bone segment 13-2 in the lateral direction. After that, all the reduction regulators are removed, and one or two external fixing needles 12 are respectively installed on the first fixing member 2 and the second fixing member 3 once again to achieve the final fixation between the retractable fixing bracket and the fractured first bone segment 13-1 and second bone segment 13-2.

The above only represents preferred embodiments of the present disclosure, but does not limit the present disclosure in any way. Any simple modification, change and equivalent structural change made to the above embodiments according to the technical essence of the present disclosure still fall within the protection scope of the present disclosure.

What is claimed is:

1. A minimally invasive fracture reduction and fixation system, comprising a retractable fixing bracket, and a reduction device and a fixing device mounted on the retractable fixing bracket, wherein the retractable fixing bracket comprises a connecting member (1), and a first fixing member (2) and a second fixing member (3) respectively mounted on both ends of the connecting member (1), the reduction device comprises at least two reduction regulators respectively mounted on the first fixing member (2) and the second fixing member (3), internal fixing needles (9) inserted into the reduction regulators and limit sleeves (10) fixedly sleeved on the internal fixing needles (9), each reduction regulator comprises an outer sleeve and an inner sleeve threadedly connected to the outer sleeve, the inner sleeve has a center hole (8-4) matching the internal fixing needle (9) at its center, and the fixing device comprises at least two external fixing needles (12) respectively mounted on the first fixing member (2) and the second fixing member (3);

by screwing the inner sleeve, the inner sleeve drives the fractured first bone segment (13-1) and second bone segment (13-2) to perform a transverse horizontal displacement in a front view; by adjusting a length of the retractable fixing bracket, the fractured first bone segment (13-1) and second bone segment (13-2) are displaced longitudinally in an anteroposterior direction; after the fractured first bone segment (13-1) and second bone segment (13-2) are reduced, the external fixing needles (12) for positioning are respectively installed on the first fixing member (2) and the second fixing member (3) in sequence, and the two external fixing needles (12) are used to realize a connection between the retractable fixing bracket and the first bone segment (13-1) and the second bone segment (13-2); after that, by adjusting the length of the retractable fixing bracket again, the two external fixing needles (12) are used to perform a final reduction between the fractured first bone segment (13-1) and second bone segment (13-2); when the final reduction meets requirements, all the internal fixing needles (9) are pulled out, all the reduction regulators are removed, and one or two external fixing needles (12) are respectively installed on the first fixing member (2) and the second fixing member (3) again to realize a final fixation between the retractable fixing bracket and the first bone segment (13-1) and the second bone segment (13-2);

wherein the outer sleeve comprises a large-diameter cylindrical sleeve section (7-1), a threaded sleeve section (7-2) and a small-diameter cylindrical sleeve section (7-3) coaxially arranged in sequence, and the threaded sleeve section (7-2) is threadedly connected to the first fixing member (2) or the second fixing member (3);

wherein the inner sleeve comprises a guide pipe section (8-1), a connecting pipe section (8-2) and a nut (8-3) coaxially arranged in sequence, and the connecting pipe section (8-2) is threadedly connected to the large-diameter cylindrical sleeve section (7-1);

wherein the internal fixing needles are selected from Kirschner wires, titanium needles or titanium pins; and wherein the external fixing needles are structurally distinct from the internal fixing needles, having at least a larger diameter than the internal fixing needles.

2. The minimally invasive fracture reduction and fixation system according to claim 1, wherein both the first fixing member (2) and the second fixing member (3) are lockable on the connecting member (1) by respective fastening bolts (4), the connecting member (1) is provided with waist-shaped holes (1-1) for the fastening bolts (4) to pass through, and the first fixing member (2) and the second fixing member (3) are each provided with a fastening bolt mounting hole (5).

3. The minimally invasive fracture reduction and fixation system according to claim 2, wherein the first fixing member (2) and the second fixing member (3) are each provided with a threaded sleeve section mounting hole (6).

4. The minimally invasive fracture reduction and fixation system according to claim 1, wherein the limit sleeve (10) is fixedly sleeved on the internal fixing needle (9) by a fastening screw (11).

* * * * *